United States Patent [19]

Kirsch et al.

[11] Patent Number: 4,586,503

[45] Date of Patent: May 6, 1986

[54] SURGICAL MICROCLIP

[75] Inventors: Wolff M. Kirsch, Albuquerque, N. Mex.; Zhu Y. Hua, Shanghai, China; Robert B. Cushman, Cedar Crest, N. Mex.

[73] Assignee: University of New Mexico, Albuquerque, N. Mex.

[21] Appl. No.: 556,917

[22] Filed: Dec. 1, 1983

[51] Int. Cl.⁴ ............................................. A61B 17/04
[52] U.S. Cl. .................................. 128/334 R; 128/346; 227/DIG. 1
[58] Field of Search ................... 128/334 R, 346, 337, 128/325, 327, 336, 326; 227/DIG. 1

[56] References Cited

U.S. PATENT DOCUMENTS

| | | | |
|---|---|---|---|
| 1,728,316 | 9/1929 | Von Wachenfeldt | 128/334 R |
| 2,201,610 | 5/1940 | Dawson, Jr. | 128/334 R |
| 2,662,524 | 12/1953 | Hudgins . | |
| 2,887,110 | 5/1959 | Roeschmann | 128/334 R |
| 3,082,426 | 3/1963 | Miles | 128/334 R |
| 3,131,448 | 5/1964 | Glatz | 128/334 R |
| 3,361,133 | 1/1968 | Kimberly et al. . | |
| 3,446,212 | 5/1969 | Le Roy . | |
| 3,604,425 | 9/1971 | Le Roy . | |
| 3,774,438 | 11/1973 | Weston . | |
| 3,775,825 | 12/1973 | Wood et al. | 128/334 R |
| 3,807,406 | 4/1974 | Rafferty et al. . | |
| 3,825,009 | 7/1974 | Williams | 128/334 R |
| 3,856,017 | 12/1974 | Perisse et al. . | |
| 3,916,909 | 11/1975 | Kletschka et al. . | |
| 3,980,086 | 9/1976 | Kletschka et al. . | |
| 4,049,002 | 9/1977 | Kletschka et al. . | |
| 4,096,864 | 6/1978 | Kletschka et al. . | |
| 4,111,206 | 9/1978 | Uishnevsky et al. | 128/334 R |
| 4,324,248 | 4/1982 | Perlin . | |
| 4,350,160 | 9/1982 | Kolesov et al. . | |
| 4,397,312 | 8/1983 | Molko | 128/334 R |
| 4,465,071 | 8/1984 | Samuels et al. | 128/334 R |

OTHER PUBLICATIONS

"The Technical Aspects of the Vascular Stapler", R. F. Mallina, Division of Instrumentation, Jan. 8, 1963, pp. 353-364.

"Surgical Stapling", R. F. Mallina et al., pp. 48-56.
"The Problem of Small Vessel Anastomosis", I. J. Vogelfanger et al., Dept. of Anatomy, Ottawa University, and the National Research Council of Canada, Div. of Mechanical Engineering, Aug. 1962, pp. 354-362.
"Microvascular Stapling", I. J. Vogelfanger et al., Ottawa pp. 39-50.
"A New Type of Vessel-Suturing Apparatus", K. Inokuchi, Fukuoka, Japan, A.M.A. Archives of Surgery, vol. 77, Dec., pp. 954-957.
"Experimental Anastomosis of the Left Internal Mammary . . . ", S. E. Carroll, Canadian Journal of Surgery, Oct. 1964, pp. 468-469.
"A Simple New Apparatus for Small Vessel Anastomosis (Free Autograft of the Sigmoid Included)", Nakayama et al., Surgery, Dec. 1962, pp. 018-931.
"The Effect of Dextran on the Incidence of Thrombosis in Microvenous Nakayama Ring Pin Anastomoses", Wiman et al., Scand J. Plast Reconstr Surg 13 pp. 263-268.
"Aorto-Pulmonary Shunt in the Premature Infant", Roe, The Journal of Thoracic and Cardiovascular Surgery, pp. 437 & 438.

(List continued on next page.)

Primary Examiner—John J. Wilson
Assistant Examiner—J. Hakomaki
Attorney, Agent, or Firm—Charles W. Fallow; Jean A. Buttmi

[57] ABSTRACT

A surgical microclip particularly adapted for microvascular anastomoses is described as including a pair of arcuate legs interconnected by a bridging section. The clip is formed of a unitary piece of biologically acceptable, plastically deformable material, and further has two spaced "ears" to facilitate handling and removal of the clip. Also disclosed is a tool for applying the clip, comprising a tweezer-like device having a pair of arms for crimping the microclip, with a fine suction conduit extending along a bisector of the angle between the arms to hold the clip prior to crimping.

4 Claims, 5 Drawing Figures

OTHER PUBLICATIONS

"A New Gearing Approximator for Microsurgical Vascular Anastomoses", E. Wintermantel, *Acta Neurochirurgica 50*, 237-242, (1979).

"Anastomosis of Small Veins with Suture or Nakayama's Apparatus", Ostrup, *Scand J. Plast Reconstr Surg 10;* 9-17, 1976.

"The Russian Stapler in Small Artery Anastomoses and Grafts", Williams et al., pp. 170-172.

"Stapler for A-V Anastomosis: Simplified, Immediate Vascular Access", Ivanovich et al., vol. XXIII *Trans. Am. Soc. Artif. Intern. Organs,* 1977, pp. 716-718.

"Suture Anastomosis of Small Arteries", Chase et al., *Surgery, Gynecology & Obstetrics,* Jul. 1963, pp. 44-46.

"Thrombogenesis in Experimental Microvascular Anastomosis", Shimizu et al., *Journal of Microsurgery,* Jul. Aug. 1979, pp. 39-49.

"A Technique of Small Artery Anastomosis", Chase et al., *Surgery, Gynecology & Obstetrics,* Mar. 1963, pp. 381-386.

"A Simple Method for Closure of the Potts Anastomosis with a Mechanical Stapler", Leand et al., *The Journal of Thoracic and Cardiovascular Surgery,* vol. 42, No. 2, Aug. 1971, pp. 285-289.

"Small Vessel Anastomosis", John Cobbett, *British Journal of Plastic Surgery,* pp. 16-20.

"A New Simple Apparatus for Anastomosis of Small Vessels", Nakayama et al., *Journal of the International College of Surgeons,* vol. 38, No. I, Jul. 1962, pp. 12-26.

"Internal Mammary-Coronary Artery Anastomosis", Goetz et al., *J. Thoracic and Cardiovas. Surg.,* vol. 41, No. 3, Mar. 1961, pp. 378-386.

"A Concept of Automation in Vascular Surgery: A Preliminary Report on a Mechanical Instrument for Arterial Anastomosis", Vogelfanger et al., *Canadian Journal of Surgery,* vol. 1, Apr. 1958, pp. 262-265.

"Stapling Device for End-to-Side Anastomosis of Blood Vessel", K. Inokuchi, M.D., Archives of Surgery, vol. 82, Mar. 1961, pp. 337-341.

"A New Method for Anastomosing Blood Vessels by Manually Applied Clips", Gonzalez et al., pp. 178-181.

"Vascular Anastomosis-Sutures, Staples or Glue?", Zingg et al., *Canad. Med. Ass. J.,* Oct. 10, 1964, vol. 91, pp. 791-794.

"Repair of Small Arteries with Contact Cement and Teflon Graft", Khodadad et al., pp. 552-560.

"New Method of Surgical Treatment of Blood Vessel Lesions", P. I. Androsov, *A.M.A. Archives of Surgery,* pp. 902-910.

"A Non-Suture Small Vessels Prosthetic Connector", Selker et al., pp. 50-52.

T. Miller, "A Preliminary Evaluation of the Androsov Stapling Device for the Circular Suture of Blood Vessels", 4-1961, pp. 216-219.

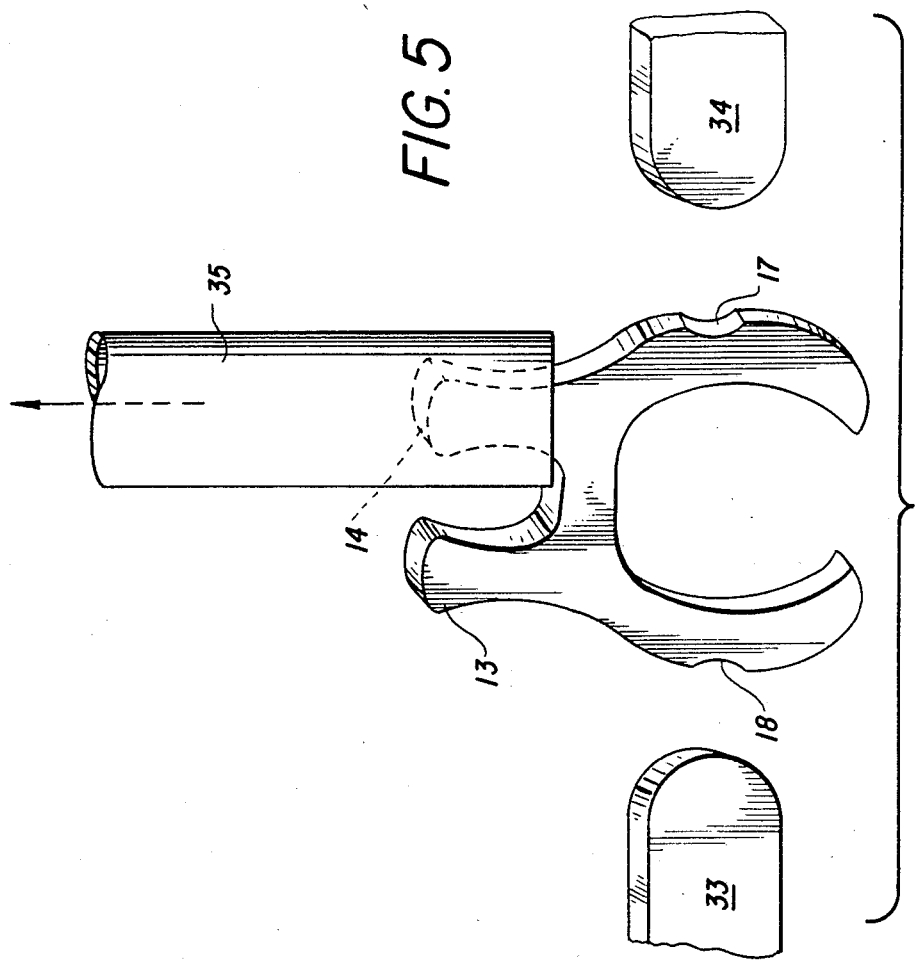

SURGICAL MICROCLIP

BACKGROUND OF THE INVENTION

This invention relates generally to the field of surgery, and more particularly to the field of vascular microsurgery.

In various surgical procedures, it is necessary to unite or reunite very small blood vessels, nerves and the like. The procedure of joining blood vessels is known as vascular anastomosis. Particularly in neurosurgical procedures and in the reattachment of severed body members, the number of anastomoses required can be very numerous, and accordingly, it is advantageous and frequently necessary to perform each such connection quickly yet properly.

A conventional end-to-end anastomosis is illustrated in FIG. 1, which shows a pair of vessels 1 and 2, each held by a respective clamp 3 or 4 while it is sutured around its circumference. The vessel ends are first approximated by inward traction on the two vascular clamps. The vessels may then be preliminarily interconnected by placing sutures at two, three or four spaced locations around the circumference of the vessel—note the threads 5 and 6 in tension—whereafter the suturing 7 is completed with a needle 8. Various suturing techniques are known, all of which are designed to: (a) provide a leak-proof connection; (b) provide adequate tensile strength; (c) avoid unnecessary restriction of the vessel; (d) avoid unnecessary tearing and other trauma to the vessel; and (e) promote rapid and thorough healing. Some of these objectives become increasingly difficult to satisfy as smaller and smaller anastomoses are carried out; furthermore, the danger of accidentally catching the rear or distal wall of a vessel with the needle as the proximal wall is being sutured increases with diminishing vessel size.

With all vascular suturing techniques, thrombosis or clotting tends to occur at the points of needle penetration. While this clotting would not usually be sufficient to occlude larger vessels, in smaller veins and arteries a significant constriction or complete occlusion of the vessel can result from clotting. In a recent article, the problem was summarized: "It is apparent to us that the damage to vascular endothelium caused by the microvascular needle perforation is considerable. The amount of subsequent platelet aggregation and clot formation can be extensive, and these platelets are known to release vasoactive substances that can alter vessel diameter. This could diminish blood flow through a 1- to 2-mm vascular anastomosis expected to give immediate increased flow to an underperfused region of the brain." D. Pagnanelli et al, *The Cutting Edge Microsurgical Needle*, Journal of Neurosurgery, volume 59, no. 3, pages 510–512 (Sept. 1983).

In addition to the physiological damage done by suturing, it is also significant that suturing, particularly of small vessels, is a very tedious time-consuming procedure which can preoccupy and fatigue a surgeon over the course of a long procedure. A more rapid way of performing microvascular anastomoses could free the surgeon for other tasks, and could shorten surgical procedures as well. The need for a workable, rapid, non-suturing technique for microsurgery is obvious.

Various non-suture devices and techniques for performing anastomoses are known, particularly for intestinal and colorectal anastomoses, for which various stapling apparatus and methods have been known for some years. Known stapling techniques, however, require penetration of the organ wall, and if applied to vascular anastomoses, the problems of clotting and the like, as described above, could be expected to arise. For vascular anastomosis, various other non-suture mechanical clamps have been suggested. Such clamps frequently include a permanent or sacrificial ferrule or the like and means for clamping the vessel against the ferrule so that penetration of the vessel wall is avoided. However, clamps of this type have not gained widespread acceptance.

In view of the foregoing, this invention has been made with a view to substantially increasing the speed of microvascular anastomoses while avoiding the clotting problems caused by conventional suturing procedures. Another object is to reduce the material costs and duration of microsurgical procedures.

A further object of the invention is to provide a permanently implantable microsurgical clip for use in place of microvascular suturing. Yet another object is to provide the surgeon with a clip that can be easily held and applied during vascular anastomoses.

This invention relates generally to a surgical procedure such as an anastomosis wherein a pair of tissues is approximated, then partially everted, and then joined by placing the legs of a microsurgical clip over the adjoined tissues and crimping the legs about the tissues in such a way as to hold the tissues together without penetrating them.

The invention is particularly directed to a microvascular surgical clip comprising a pair of arcuate legs interconnected by a bridging section and extending in a common direction therefrom, the clip being made of a biologically acceptable material such as a noble metal, which material further must be capable of plastic deformation so that the legs can be crimped together around a pair of adjoined biological tissues. The clip preferably includes also a pair of ears extending from the bridging section in a direction opposite that of the legs. One can spread the legs and thereby release the tissues by applying inward force on the outside of the ears. Furthermore, each ear constitutes a convenient means by which the clip may be held, preferably by a vacuum conduit.

To illustrate the clip application procedure and the usefulness of the ears, also disclosed herein is a tool or tweezers for applying the inventive clip. The tool comprises a pair of interconnected arms capable of pivoting motion with respect to one another. Each arm is curved inwardly at its lower end with the distal portions of the arms directed substantially at one another so that one can crimp a microsurgical clip between the jaws of the tool by applying inward pressure on the arms. A fine suction conduit, connected to the tool and extending generally along a bisector of the two arms, terminates slightly above the point of closure of the distal ends of the arms. The inside diameter of the tube is sized to fit over one of the clip ears whereby the clip can be retained indefinitely at the distal end of the tube by the vacuum therein. This facilitates manipulation of the clip in the surgical field as the clip is positioned astride abutting tissues and then crimped.

The invention is illustrated by the following description of a preferred embodiment and by the drawings wherein FIG. 1 shows a prior art suturing procedure described above; FIG. 2 is an oblique view of the inventive microvascular surgical clip in its original position; FIG. 3 is a view similar to FIG. 2 showing the clip in its crimped position; FIG. 4 is a profile view of a tool for applying the microsurgical clip; and FIG. 5 is a view at an enlarged scale of a portion of FIG. 4.

DESCRIPTION OF THE PREFERRED EMBODIMENT

Figure 2:
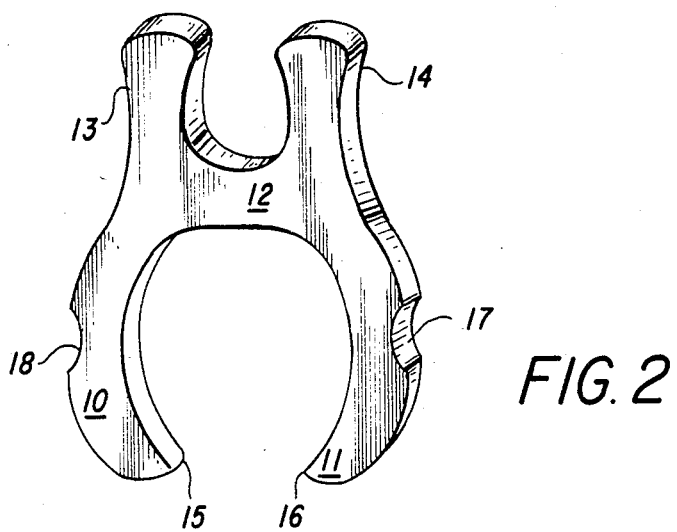

As shown in FIG. 2, a surgical microclip embodying the invention is formed of a unitary piece of biologically acceptable, plastically deformable material such as a noble metal (i.e. gold, silver, platinum, etc.) While metal clips are presently preferred, it is contemplated that other materials such as suitable polymer plastics may be used. Whatever the material, it must be sufficiently ductile or plastically deformable so that when the clip is crimped there is minimal spring-back. Otherwise, possible injurious overcrimping, to compensate for the spring-back, would be required.

Structurally, the clip includes a pair of inwardly curved legs 10 and 11 interconnected by a bridging section 12, the two legs extending generally parallel in one direction from the bridging section. The legs terminate at tips 15 and 16 which are rounded to prevent injury to the subject tissue in accordance with an object of this invention. The outer side of each leg near its mid-point is provided with a detent 17 or 18 for receiving the jaws of an applicator tool. Preferably, the clip further includes a pair of spaced ears 13 and 14 extending from the bridging section in a direction generally opposite that of the legs; however, the ears may not be neccessary or desirable for certain applications, and earless clips are within the ambit of the invention in its broadest sense.

The size of the clip will naturally vary according to the application, and it is not intended to limit the scope of this invention to any particular size clip. However, for the sake of illustration, for the anastomosis of a 1-mm vessel an appropriate size clip has an overall height on the order of 0.030 inches and an overall thickness on the order of 0.006 inches. For this size clip, the radius of curvature of the tip of each leg is approximately 0.001 inches, and the radius of each detent is about 0.010 inches.

Figure 1:
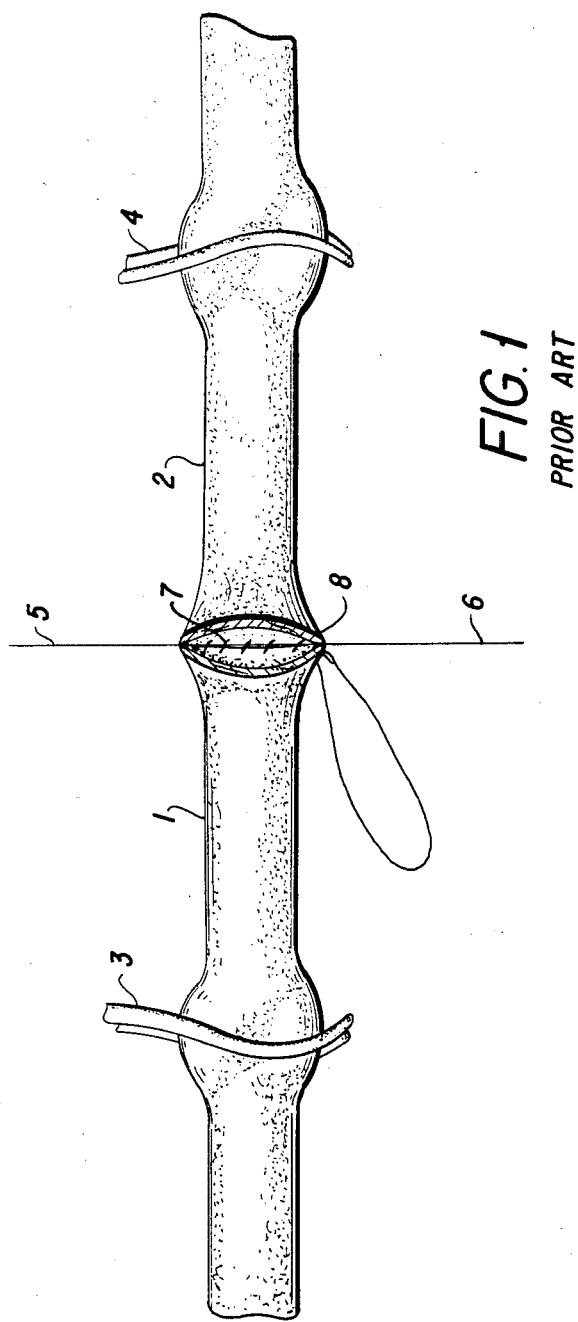
Figure 3:
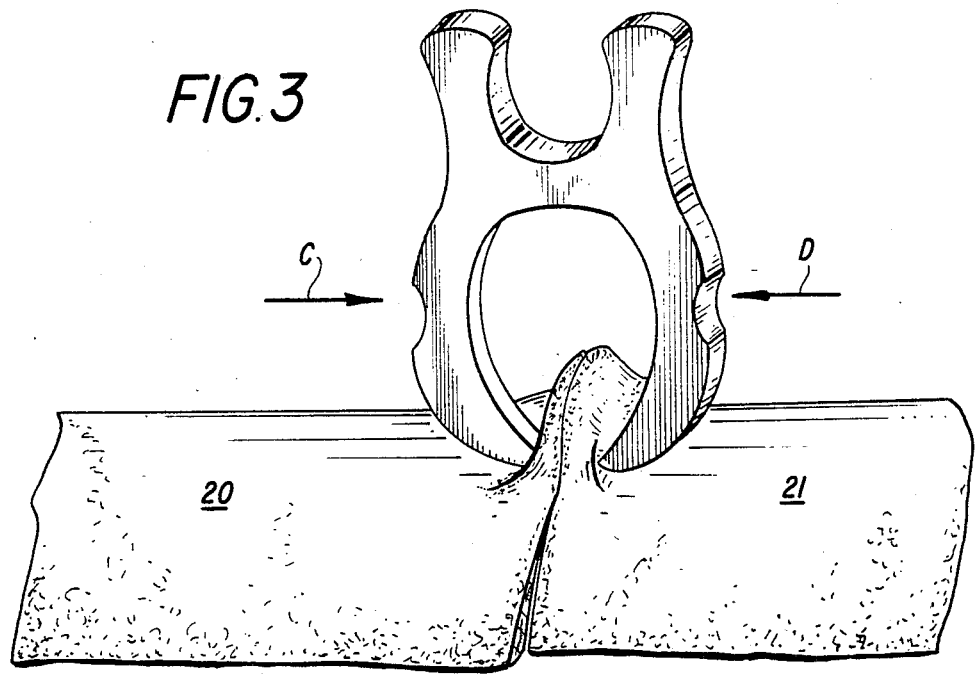
Figure 4:
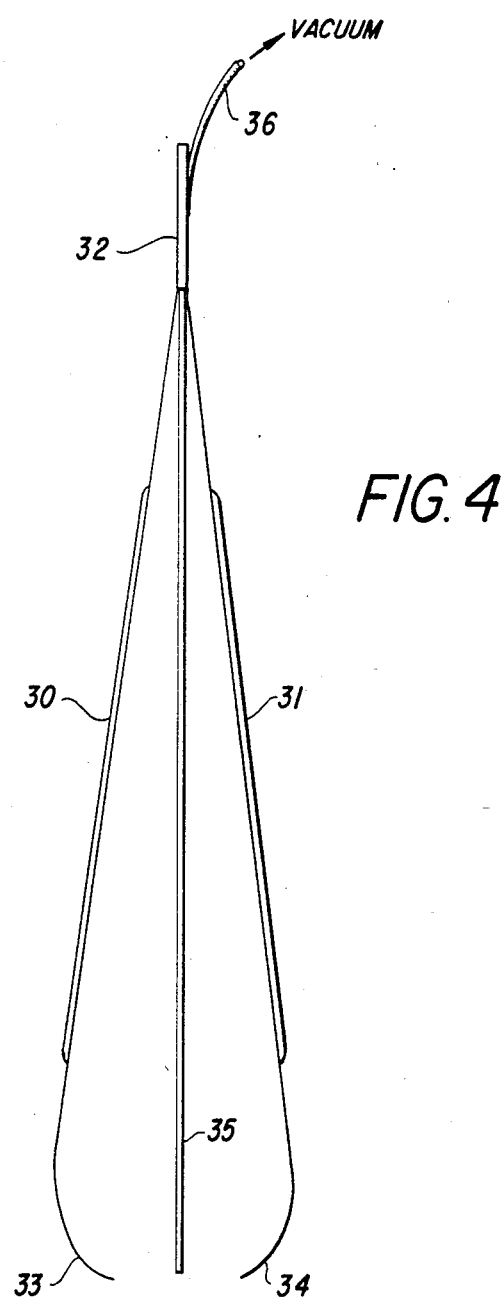

FIG. 3 illustrates the shape of the clip once it has been deformed by crimping. Note that most or all of the permanent deformation occurs in the bridge section 12 rather than the legs 10 and 11. Arrows C and D illustrate points at which inward force is applied when crimping the clip in place over a pair of adjoined membranes, which are designated by the reference numerals 20 and 21. These membranes could be the partially everted outer walls of a blood vessel, as illustrated in FIG. 1, but inasmuch as the usefulness of the invention is not limited to anastomoses, the illustrated membranes could be non-vascular FIG. 4 illustrates a tweezer-type tool for holding and crimping the microclips described above. The tool comprises two arms 30 and 31 which are resiliently interconnected at a head or handle 32. The distal ends of the arms are curved inwardly towards each other, terminating at tips 33 and 34 having roughly the same radius of curvature as the detents 17 and 18 they are intended to engage. In order to hold the microclips in position prior to crimping, a vacuum conduit 35 is provided, which conduit is of very small diameter and extends generally along a bisector of the angle between the arms 30 and 31. In FIG. 4, a microclip is illustrated at the bottom end of conduit 35, and this portion of the Figure is enlarged at FIG. 5.

FIG. 5 shows the lower end of the conduit 35, the arrow indicating the direction of a source of vacuum. As shown, a clip has been positioned at the bottom of the tube with one of the ears actually in the tube; the vacuum retains the clip in this position while it is being applied, thereby minimizing the likelihood of losing a clip within the surgical field.

In use, a pair of tissues to be joined are first drawn together in apposition (approximated) by suitable means. The edges of the tissues should be partially everted, that is, pursed outwardly, so that a clip can be placed over the tissue edges, with the legs of the clip astride the point of apposition. Once the clip has been positioned properly with respect to the subject tissues, crimping is effected simply by squeezing together the arms 30 and 31 of the tool. This causes permanent deformation of the microclip bridge section 12, whereafter the clip retains the tissues in apposition without puncturing them. This procedure is repeated at as many points as needed to fully join the subject tissues. The clips, being biologically inert, ordinarily may be left in place permanently. However, in the event that the clip must be removed, a plier tool or the like may be used to force the ears 13 and 14 together, thereby spreading the legs 10 and 11 and releasing the tissue therebetween.

The microclip and applier tool described above provide a sutureless means for the apposition of tissue which is substantially faster than conventional suturing methods, particularly in microvascular anastomosis and which avoids the clotting problem caused by needle perforations. In testing on femoral arteries in rats, short and long term patency and remarkably little damage to the vascular endothelium have been observed.

An advantage of microclips over sutures is the predictability of results. In contrast to hand-made microsuturing needles, the mass-produced microclips are uniform, producing more uniform results.

An additional advantage is that the speed of application reduces the time blood supply is interrupted, enhancing prospects for vessel patency.

It should be understood that the foregoing description and drawings describe and illustrate but one embodiment of the invention, whose scope should be measured by the following claims.

We claim:

1. A surgical microclip comprising
a bridge portion, and
a pair of spaced legs extending generally parallel from opposite ends of said bridge,
a pair of ears extending generally parallel from opposite ends of said bridge in a direction opposite that of said legs, whereby said ears facilitate manipulation of said clip prior to placement and further provide means for opening said clip if removal is desired,
said clip being constructed of a biologically acceptable, plastically deformable material whereby the clip may be permanently deformed by crimping to close said legs around approximated body tissues to hole the same together, and
said legs terminating at distal tips, said tips being sufficiently rounded to avoid puncturing or otherwise injuring said tissues.

2. A clip as described in claim 1, wherein said legs are arcuate, the concave sides of the legs facing one another.

3. A surgical technique for the apposition of tissues comprising
approximating the edges of said tissues, partially everting said edges, positioning a plastically deformable clip over said edges, and crimping said clip so as to clamp said edges together without penetrating the tissues.

4. A microvascular anastomosis technique comprising steps of aligning two vessels, approximating said vessels and simultaneously partially everting the ends of said vessels, positioning a deformable clip having spaced legs over said edges with the legs astride both everted edges, crimping said clip sufficiently to clamp said edges together between said legs but without penetrating the walls of said vessels, and repeating the everting, positioning and crimping steps around the approximated edges of the vessels to complete the anastomosis.

* * * * *